United States Patent [19]

Wächtler et al.

[11] Patent Number: 5,167,859
[45] Date of Patent: Dec. 1, 1992

[54] 2,5-DISUBSTITUTED HETEROCYCLE AND LIQUID-CRYSTALLINE PHASE

[75] Inventors: Andreas Wächtler, Griesheim; Thomas Geelhaar, Mainz; Hans-Adolf Kurmeier, Seeheim-Jugenheim; Detlef Pauluth, Darmstadt, all of Fed. Rep. of Germany

[73] Assignee: Merck Patent Gesellschaft Mit Beschraenkter Haftung, Darmstadt, Fed. Rep. of Germany

[21] Appl. No.: 454,479

[22] Filed: Dec. 21, 1989

[30] Foreign Application Priority Data

Dec. 22, 1988 [DE] Fed. Rep. of Germany ....... 3843128

[51] Int. Cl.$^5$ .................... C09K 19/34; G02F 1/13; C07D 213/26
[52] U.S. Cl. ........................ 252/299.61; 252/299.01; 546/339; 359/104
[58] Field of Search ............ 252/299.01, 299.61; 359/104; 546/339

[56] References Cited

U.S. PATENT DOCUMENTS

| | | | |
|---|---|---|---|
| 4,723,018 | 2/1988 | Shionozaki et al. | 546/342 |
| 4,781,857 | 11/1988 | Inoue et al. | 252/299.61 |
| 4,795,587 | 1/1989 | Ohno et al. | 252/299.61 |
| 4,898,455 | 2/1990 | Buchecker et al. | 356/350 R |

Primary Examiner—Robert L. Stoll
Assistant Examiner—Shean C. Wu
Attorney, Agent, or Firm—Millen, White, Zelano and Branigan

[57] ABSTRACT

2,5-Disubstituted heterocycles of the formula I

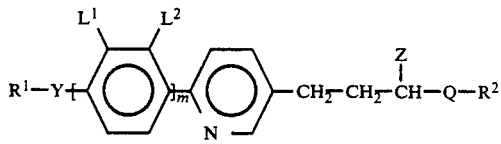

in which $R^1$ and $R^2$, each independently of one another, are alkyl, alkenyl or oxaalkyl having up to 12 C atoms,
$L^1$ and $L^2$, each independently of one another are H or F,
Y is —O—, —CO—O—, —O—CO— or a single bond,
m is 1 or 2,
Z is H, F, OH or alkyl having up to 5 C atoms, and
Q is —O—, —O—CO—, or if Z is fluorine or hydroxyl, is also be a single bond are suitable as components of ferroelectric mixtures.

8 Claims, No Drawings

2,5-DISUBSTITUTED HETEROCYCLE AND LIQUID-CRYSTALLINE PHASE

SUMMARY OF THE INVENTION

The invention relates to a 2,5-disubstituted heterocycle of the formula I

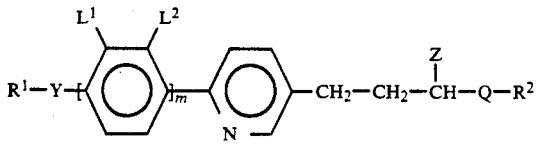

in which $R^1$ and $R^2$, each independently of one another, are alkyl, alkenyl or oxaalkyl having up to 12 C atoms, $L^1$ and $L^2$, each independently of one another, are H or F, Y is —O—, —CO—O—, —O—CO— or a single bond, m is 1 or 2, z is H, F, OH or alkyl having up to 5 C atoms, and Q is —O—, —O—CO—, or if Z is fluorine or hydroxyl, is also a single bond.

The compounds of the formula I, like similar compounds described in German Offenlegungsschrift 3,515,373 and German Offenlegungsschrift 3,515,374 can be used as components of chiral tilted smectic liquid-crystalline phases.

Chiral tilted smectic liquid-crystalline phases having ferroelectric properties can be prepared by adding a suitable chiral doping substance to basis mixtures containing one or more tilted smectic phases (L. A. Beresnev et al., Mol. Cryst. Liq. Cryst. 89, 327 (1982); H. R. Brand et al., J. Physique 44, (lett.), 1-771 (1983)). These phases can be used as dielectrics for rapidly switching displays which are based on the principle of SSFLC technology described by Clark and Lagerwall (N. A. Clark and S. T. Lagerwall, Appl. Phys. Lett. 36. 899 (1980); U.S. Pat. No. 4,367,924), which is based on the ferroelectric properties of the chiral tilted phase. In this phase, the elongate molecules are arranged in layers in which the molecules have a tilt angle perpendicular to the layer. The tilt direction changes from layer to layer by a small angle with respect to an axis which is perpendicular to the layers, leading to the formation of a helical structure. In displays which are based on the principle of SSFLC technology, the smectic layers are arranged perpendicular to the plates of the cell. The helical arrangement of the tilt directions of the molecules is suppressed by means of a very small spacing of the plates (about 1-2 μm). This forces the longitudinal axes of the molecules to align in a plane parallel to the plates of the cell, as a result of which two preferred tilt orientations are formed. By applying a suitable electric alternating field, it is possible in the liquid-crystalline phase which exhibits spontaneous polarization to switch back and forth between these two states. This switching process is considerably faster than in conventional twisted cells (TN-LCDs) which are based on nematic liquid crystals.

A great disadvantage for many applications of the presently available materials having chiral tilted smectic phases (for example Sc*) is their relatively high optical anisotropy, switching times which are not sufficiently short due to relatively high viscosity values, and dielectric anisotropy having values of greater than zero or, if negative, values which differ only slightly from zero. Negative values of the dielectric anisotropy are required if the required plane orientation is caused by superposition of the control field on an AC holding field which has a small amplitude (J. M. Geary, SID Congress, Orlando/Fla. Apr./May 1985, Talk 8.3). Finally, the temperature-dependency of the switching times of the presently available ferroelectric mixtures is so high that in many cases electronic compensation is required.

It has now been found that the use of compounds of the formula I as components of chiral tilted smectic mixtures can significantly reduce the disadvantages mentioned. Accordingly, the compounds of the formula I are highly suitable as components of chiral tilted smectic liquid-crystalline phases. In particular, they are suitable for preparing chemically particularly stable chiral tilted smectic liquid-crystalline phases having favorable ferroelectric phase ranges, in particular having broad Sc* phase ranges, negative or even positive dielectric anisotropy, low optical anisotropy, favorable pitch level low viscosity, particularly low temperature dependency of the switching times and, for such phases, high values for spontaneous polarization and very short switching times. P is the spontaneous polarization in $nC/cm^2$.

Moreover, by providing the compounds of the formula I the range of liquid-crystalline substances which are suitable in various technical aspects for the preparation of ferroelectric mixtures is quite considerably widened.

The compounds of the formula I have a wide range of application. Depending on the selection of the substituents, these compounds can be used as basis materials from which liquid-crystalline phases are predominantly composed; however, it is also possible to add liquid-crystalline basis materials from other classes of compounds to the compounds of the formula I, in order to vary, for example, the dielectric and/or optical anisotropy and/or spontaneous polarization and/or phase range and/or tilt angle and/or pitch and/or switching times of such a phase. The compounds of the formula I are furthermore suitable as intermediates for the preparation of other substances which can be used as components of liquid-crystalline phases.

The compounds of the formula I are colorless in their pure state and have favorable values of optical anisotropy. Some of the compounds of the formula I have liquid-crystalline mesophases in a temperature range which is favorable for electrooptical use; however, it can also be advantageous to use isotropic or monotropic liquid-crystalline compounds of the formula I as components of chiral tilted smectic phases. They have very good chemical, heat and light stability.

The invention accordingly relates to the compounds of the formula I and to the use of the compounds of the formula I as components of liquid-crystalline phases.

The invention also relates to chiral tilted smectic liquid-crystalline phases containing at least one compound of the formula I.

The invention also relates to electrooptical display elements which contain these type of phases.

Above and below, $R^1$, $R^2$, m, $L^1$, $L^2$, Y, Z and Q have the meaning given unless expressly stated otherwise.

The compounds of the formula I accordingly comprise in particular compounds of the partial formulae Ia R¹—Y—⟨ring(L¹,L²)⟩—⟨ring(N)⟩—CH₂CH₂—CH(Z)—Q—R²

Ib

R¹—Y—⟨ring(L¹,L²)⟩—⟨ring(L¹,L²)⟩—⟨ring(N)⟩—CH₂CH₂—CH(Z)—Q—R²

Ic

R¹—Y—[⟨ring(L¹,L²)⟩]ₘ—⟨ring(N)⟩—CH₂CH₂—CH(F)—R²

Id

R¹—Y—[⟨ring(L¹,L²)⟩]ₘ—⟨ring(N)⟩—CH₂CH₂—CH(OH)—R²

Of these, those of the formula Ia are particularly preferred.

Compounds of the formulae above and below which have branched wing groups R¹ or R² can be of importance. Branched groups of this type usually contain no more than two chain branchings. R¹ is preferably a straight-chain group or a branched group containing no more than one chain branching.

Preferred branched radicals are isopropyl, 2-butyl (=1-methylpropyl), isobutyl (=2-methylpropyl), tert.-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl.

The radical R¹ and in particular also the radical R² can also be an optically active organic radical having an asymmetric carbon atom.

R¹ and R² are preferably alkyl or alkenyl having up to 12 C atoms. Alkyls having 2 to 12 C atoms, i.e. ethyl, propyl, butyl, pentyl, hexyl, heptyl, octyl, nonyl, decyl, undecyl and dodecyl are particularly preferred. These groups can be straight-chain or branched, straight-chain alkyl groups being preferred. However, R² is also preferably methyl or branched alkyl having a methyl branching, e.g. isopropyl.

Y is preferably —O— or —CO—O—, particularly preferably —O—.

m is preferably 1.

The radical

—[⟨ring(L¹,L²)⟩]ₘ— preferably has one of the following meanings 1 to 6:

1. ⟨phenyl⟩
2. ⟨phenyl⟩—⟨phenyl⟩
3. ⟨phenyl with F⟩
4. ⟨phenyl with F⟩
5. ⟨phenyl with F,F⟩
6. ⟨phenyl⟩—⟨phenyl with F⟩

The meanings 1 and 2, in particular 1, are particularly preferred. The position of fluorine in 6 is as desired. Specifically, the fluorine atom may be substituted in any of the 2- or 3-positions on either ring.

The preferred compounds in which Z is alkyl having up to 5 C atoms are preferably optically active and are used as chiral doping substances for ferroelectric mixtures. Z is preferably methyl, ethyl, n-propyl or isopropyl. Methyl is particularly preferred.

The particularly preferred compounds in which Z is fluorine are preferably optically active and are used as chiral doping substances for ferroelectric mixtures. Q is in this case preferably a single bond and R² is preferably straight-chain or branched alkyl having up to 10 C atoms, preferably having 3 to 8 C toms.

The preferred compounds in which Z is OH are interesting intermediates, in particular for liquid crystals. Q is in this case preferably a single bond and R² is preferably straight-chain or branched alkyl having up to 10 C atoms, preferably having 3 to 8 C atoms.

The preferred compounds in which Z is H are preferably achiral basis materials for ferroelectric mixtures. Q is in this case —O— or -0—CO-.

Of the compounds of the formula I and Ia to Id, those are preferred in which at least one of the radicals present has one of the preferred meanings mentioned.

The compounds of the formula I are prepared by methods known per se, such as are described in the literature (e.g. in the standard works such as HoubenWeyl, Methoden der Organischen Chemie (Methods of Organic Chemistry), Georg-Thieme Verlag, Stuttgart), under reaction conditions which are known and suitable for the reactions mentioned. It is also possible to use variations known per se and not mentioned here in more detail.

If desired, it is also possible to form the starting materials in situ, such that they are not isolated from the reaction mixture but are immediately further reacted to the compounds of the formula I.

Thus, the compounds of the formula I or suitable precursors for their preparation can be prepared by reacting a compound of the formula I'

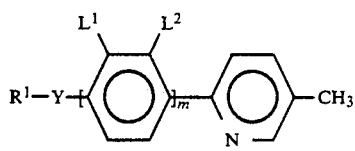

in which $R^1$, Y, $L^1$, $L^2$, and m have the abovementioned meaning or a suitable precursor under basic conditions with an epoxide of the formula II

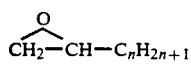

in which n is 0 to 12. If n is 1 to 12, an optically active epoxide is preferably used. This gives the compounds according to the invention of the formula Id or, if ethylene oxide is used, the likewise still novel intermediates of the formula Ie

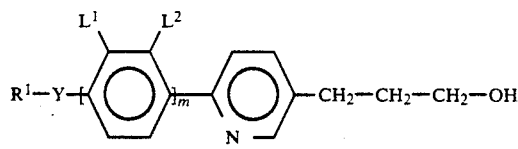

which are also provided by the present invention and in which $R^1$, Y, $L^1$, $L^2$, and m have the abovementioned preferred meanings.

The reaction conditions of the reaction of I' with epoxides are not critical per se. The 2-substituted 5-methylpyridines of the formula I' are metallated under the conditions mentioned in DE 3,632,411 (Example 3)(it being possible to omit the use of DMPU), and an equimolar amount of a chiral or nonchiral epoxide of the formula II is then added at −10° C. The epoxide is opened regioselectively at the less substituted C atom to give the corresponding (optically active) alcohols, which can be converted with inversion to the fluorine compounds of the formula Ic according to the invention by means of DAST (dimethylaminosulfur trifluoride) (M. Hudlicky, Organic Reactions 35, 513–637 (1988)). Etherification or esterification of the alcohols under the conditions customary in the literature gives the ethers and esters of the formula Ia and Ib according to the invention.

The starting materials of the formula II are known or available in analogy to known compounds. Various compounds of the formula II are commercially available. The starting materials of the formula I' are available from 2-p-methoxyphenyl-5-methylpyridine by basic ether cleavage using K tert.-butoxide in N-methylpyrrolidone (NMP) at 150°–200° C. and subsequent repeated etherification with the corresponding alkyl halides or by cross-coupling of the corresponding aromatic boronic acids with 2-bromo-5-methylpyridine according to M. J. Sharp, W. Cheng and V. Snieckus, Tetrahedron Letters 28, 5093 (1987).

The phases according to the invention contain at least one, preferably at least two, compounds of the formula I. Chirally tilted smectic liquid-crystalline phases according to the invention whose achiral basis mixture contains, in addition to compounds of the formula I, at least one other component which has a negative or, in terms of the absolute magnitude, small positive dielectric anisotropy are particularly preferred. The chirality is preferably based in part or completely on chiral compounds of the formula I. These phases preferably contain one or two chiral compounds of the formula I. However, it is also possible to use achiral compounds of the formula I (for example in the form of a racemate), in which case the chirality of the phase is then caused by other optically active compounds. If chiral compounds of the formula I are used, in addition to the pure optical antipodes, mixtures which have an enantiomeric excess are also suitable. The abovementioned further component(s) of the achiral basis mixture can amount to 1 to 50%, preferably 10 to 25%, of the basis mixture.

The compounds of the formula I are also suitable as components of nematic liquid-crystalline phases, e.g. for avoiding reverse twist.

These liquid-crystalline phases according to the invention consist of 2 to 25, preferably 3 to 15, components, of which at least one is a compound of the formula I. The other components are preferably selected from the nematic or nematogenic substances, in particular the known substances, from the classes of azoxybenzenes, benzylideneanilines, biphenyls, terphenyls, phenyl- or cyclohexylbenzoates, phenylcyclohexanecarboxylates or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis(cyclohexyl)biphenyls, phenyl- or cyclohexylpyrimidines, phenyl- or cyclohexylpyridazines and their N-oxides, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, halogenated or non-halogenated stilbenes, benzyl phenyl ethers, tolans and substituted cinnamic acids.

The most important compounds suitable as components of these liquid-crystalline phases can be described by the formula I'

$$R'—L—G—E—R''$$   I' in which L and E are each a carbocyclic or heterocyclic ring system from the group consisting of 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline. G is

| —CH=CH— | —N(O)=N— |
| —CH=CY— | —CH=N(O)— |
| —C≡C— | —CH₂—CH₂— |
| —CO—O— | —CH₂—O— |
| —CO—S— | —CH₂—S— |
| —CH=N— | —COO—Phe—COO— | or a C—C single bond, Y is halogen, preferably chlorine, or —CN, and R' and R" are alkyl, alkoxy, alkanoyloxy, alkoxycarbonyl or alkoxycarbonyloxy having up to 18, preferably up to 8, carbon atoms, or one of these radicals is also CN, $NO_2$, $CF_3$, F, Cl or Br.

In most of these compounds, R' and R" are different from one another, one of these radicals being in most cases an alkyl or alkoxy group. However, other variations of the intended substituents are also customary. Many of these substances or even mixtures thereof are commercially available. All these substances are available by methods known in the literature.

The phases according to the invention contain about 0.1 to 99, preferably 10 to 95%, of one or more compounds of the formula I. Liquid-crystalline phases according to the invention which contain 0.1–40, preferably 0.5–30%, of one or more compounds of the formula I are furthermore preferred.

The preparation of the phases according to the invention is carried out in a manner customary per se. As a rule, the components are dissolved in one another, advantageously at elevated temperature. The liquid-crystalline phases can be modified according to the invention by means of suitable additives in such a manner that they can be used in all previously known types of liquid crystal display elements.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application Federal Republic of Germany P 38 43 128.9, filed Dec. 22, 1988, are hereby incorporated by reference.

M.P.=melting point, c.p.=clear point. "Customary work-up" means: water is added, the mixture is extracted with methylene chloride, the organic phase is separated off, dried and evaporated, and the product is purified by crystallization and/or chromatography.

Furthermore C denotes crystalline solid state, S denotes smectic phase (the index designates the phase type), N denotes nematic state, Ch cholesteric phase, I isotropic phase. The number between two symbols indicates the conversion temperatures in degrees centigrade.

EXAMPLES

Example 1

In the absence of moisture and in an $N_2$ atmosphere, 70 ml of a solution of n-BuLi in hexane are added to a solution of 90 ml of THF (tetrahydrofuran) and 15.6 ml of diisopropylamine at about $-40°$ C., and 29.7 g of 2-p-octyloxyphenyl-5-methylpyridine dissolved in 100 ml of THF are then added to the mixture at the same temperature. The reaction mixture is stirred at $-10°$ C. for 30 minutes, and 12.8 g of optically active 1,2-epoxyoctane dissolved in 20 ml of THF are then added. The mixture is then stirred at room temperature for 3 hours and worked up as usual. This gives optically active 2-p-octyloxyphenyl-5-(3-hydroxynonyl)pyridine.

The following are prepared analogously:

2-p-nonyloxyphenyl-5-(3-hydroxynonyl)pyridine
2-p-decyloxyphenyl-5-(3-hydroxynonyl)pyridine
2-p-undecyloxyphenyl-5-(3-hydroxynonyl)pyridine
2-p-dodecyloxyphenyl-5-(3-hydroxynonyl)pyridine
2-p-(1,4-dioxanonyl)-phenyl-5-(3-hydroxynonyl)pyridine
2-p-(7-octenyloxy)-phenyl-5-(3-hydroxynonyl)pyridine
2-(4-octyloxybiphenyl-4'-yl)-5-(3-hydroxynonyl)pyridine
2-(3-fluoro-4-octyloxy)-phenyl-5-(3-hydroxynonyl)pyridine
2-(2-fluoro-4-octyloxy)-phenyl-5-(3-hydroxynonyl)pyridine
2-p-octanoyloxyphenyl-5-(3-hydroxynonyl)pyridine

Example 2

5 ml of DAST dissolved in 10 ml of dichloromethane are added dropwise at $-20°$ C. in the absence of moisture to a solution of 10.6 g of optically active 2-p-octyloxyphenyl-5-(3-hydroxynonyl)pyridine in 70 ml of dichloromethane. After the reaction is completed, the reaction mixture is poured into ice water and worked up as usual. This gives optically active 2-p-octyloxyphenyl-5-(3-fluorononyl)pyridine, C 66 $S_I^*$ 73 $S_c^*$ 86 $S_A$ 90 I.

The following are prepared analogously:
2-p-octyloxyphenyl-5-(3-fluorobutyl)pyridine
2-p-octyloxyphenyl-5-(3-fluoropentyl)pyridine
2-p-octyloxyphenyl-5-(3-fluorohexyl)pyridine
2-p-octyloxyphenyl-5-(3-fluoroheptyl)pyridine
2-p-octyloxyphenyl-5-(3-fluorooctyl)pyridine
2-p-octyloxyphenyl-5-(3-fluorodecyl)pyridine
2-p-octyloxyphenyl-5-(3-fluoroundecyl)pyridine
2-p-octyloxyphenyl-5-(3-fluorododecyl)pyridine
2-p-hexyloxyphenyl-5-(3-fluorobutyl)pyridine
2-p-hexyloxyphenyl-5-(3-fluoropentyl)pyridine
2-p-hexyloxyphenyl-5-(3-fluorohexyl)pyridine
2-p-decyloxyphenyl-5-(3-fluorododecyl)pyridine
2-p-decyloxyphenyl-5-(3-fluoro-4-methylpentyl)pyridine
2-(3-fluoro-4-octyloxyphenyl-5-(3-fluorobutyl)pyridine
2-(3-fluoro-4-octyloxyphenyl-5-(3-fluoropentyl)pyridine
2-(3-fluoro-4-octyloxyphenyl-5-(3-fluorohexyl)pyridine
2-(3-fluoro-4-octyloxyphenyl-5-(3-fluoroheptyl)pyridine
2-(3-fluoro-4-octyloxyphenyl-5-(3-fluorooctyl)pyridine
2-(3-fluoro-4-octyloxyphenyl-5-(3-fluorononyl)pyridine
2-(3-fluoro-4-octyloxyphenyl-5-(3-fluorodecyl)pyridine
2-(3-fluoro-4-octyloxyphenyl-5-(3-fluoroundecyl)pyridine
2-(3-fluoro-4-octyloxyphenyl-5-(3-fluorododecyl)pyridine
2-(3-fluoro-4-octyloxyphenyl-5-(3-fluoro-4-methylpentyl)pyridine
2-(2,3-difluoro-4-octyloxyphenyl-5-(3-fluorobutyl)pyridine
2-(2,3-difluoro-4-octyloxyphenyl-5-(3-fluoropentyl)pyridine
2-(2,3-difluoro-4-octyloxyphenyl-5-(3-fluorohexyl)pyridine
2-(2,3-difluoro-4-octyloxyphenyl-5-(3-fluoroheptyl)pyridine
2-(2,3-difluoro-4-octyloxyphenyl-5-(3-fluorooctyl)pyridine
2-(2,3-difluoro-4-octyloxyphenyl-5-(3-fluorononyl)pyidine
2-(2,3-difluoro-4-octyloxyphenyl-5-(3-fluorodecyl)pyridine 2-(2,3-difluoro-4-octyloxyphenyl-5-(3-fluoroundecyl)-pyridine
2-(2,3-difluoro-4-octyloxyphenyl-5-(3-fluorododecyl)-pyridine
2-(2,3-difluoro-4-octyloxyphenyl-5-(3-fluoro-4-methylpentyl)pyridine

Example 3

Esterification of optically active 2-p-octyloxyphenyl-5-(3-hydroxybutyl)pyridine [available analogously to Example 1 by reaction of 2-p-octyloxyphenyl-5-methylpyridine with chiral propylene oxide] with n-pentanoic acid gives 2-p-octyloxyphenyl-5-(3-pentanoyloxybutyl)pyridine, C 37 I.

Example 4

Etherification of 2-p-octyloxyphenyl-5-(3-hydroxypropyl)pyridine [available analogously to Example 1 by reacting 2-p-octyloxyphenyl-5-methylpyridine with ethylene oxide] with n-butyl bromide gives 2-p-octyloxyphenyl-5-(4-oxaoctyl)pyridine.

The following are prepared analogously:
2-p-octyloxyphenyl-5-(4-oxaheptyl)pyridine
2-p-octyloxyphenyl-5-(4-oxanonyl)pyridine
2-p-octyloxyphenyl-5-(4-oxadecyl)pyridine
2-p-octyloxyphenyl-5-(4-oxauniecyl)pyridine
2-p-octyloxyphenyl-5-(4-oxadodecyl)pyridine
2-p-nonyloxyphenyl-5-(4-oxapentyl)pyridine
2-p-nonyloxyphenyl-5-(4-oxahexyl)pyridine
2-p-nonyloxyphenyl-5-(4-oxaheptyl)pyridine
2-p-nonyloxyphenyl-5-(4-oxaoctyl)pyridine
2-p-nonyloxyphenyl-5-(4-oxanonyl)pyridine
2-p-nonyloxyphenyl-5-(4-oxadecyl)pyridine
2-p-nonyloxyphenyl-5-(4-oxaundecyl)pyridine
2-p-nonyloxyphenyl-5-(4-oxadodecyl)pyridine
2-p-nonyloxyphenyl-5-(4-oxa-6-methyloctyl)pyridine
2-p-decyloxyphenyl-5-(4-oxapentyl)pyridine
2-p-decyloxyphenyl-5-(4-oxahexyl)pyridine
2-p-decyloxyphenyl-5-(4-oxaheptyl)pyridine
2-p-decyloxyphenyl-5-(4-oxaoctyl)pyridine
2-p-decyloxyphenyl-5-(4-oxanonyl)pyridine
2-p-decyloxyphenyl-5-(4-oxadecyl)pyridine
2-p-decyloxyphenyl-5-(4-oxaundecyl)pyridine
2-p-decyloxyphenyl-5-(4-oxadodecyl)pyridine
2-p-decyloxyphenyl-5-(4-oxa-6-methyloctyl)pyridine
2-p-dodecyloxyphenyl-5-(4-oxapentyl)pyridine
2-p- dodecyloxyphenyl-5-(4-oxahexyl)pyridine
2-p-dodecyloxyphenyl-5-(4-oxaheptyl)pyridine
2-p-dodecyloxyphenyl-5-(4-oxaoctyl)pyridine
2-p-dodecyloxyphenyl-5-(4-oxanonyl)pyridine
2-p-dodecyloxyphenyl-5-(4-oxadecyl)pyridine
2-p-dodecyloxyphenyl-5-(4-oxaundecyl)pyridine
2-p-dodecyloxyphenyl-5-(4-oxadodecyl)pyridine
2-p-dodecyloxyphenyl-5-(4-oxa-6-methyloctyl)pyridine
2-p-heptyloxyphenyl-5-(4-oxapentyl)pyridine
2-p-heptyloxyphenyl-5-(4-oxahexyl)pyridine
2-p-heptyloxyphenyl-5-(4-oxaheptyl)pyridine
2-p-heptyloxyphenyl-5-(4-oxaoctyl)pyridine
2-p-heptyloxyphenyl-5-(4-oxanonyl)pyridine
2-p-heptyloxyphenyl-5-(4-oxadecyl)pyridine
2-p-heptyloxyphenyl-5-(4-oxaundecyl)pyridine
2-p-heptyloxyphenyl-5-(4-oxadodecyl)pyridine
2-p-heptyloxyphenyl-5-(4-oxa-6-methyloctyl)pyridine
2-hexyloxyphenyl-5-(4-oxapentyl)pyridine
2-hexyloxyphenyl-5-(4-oxahexyl)pyridine
2-hexyloxyphenyl-5-(4-oxaheptyl)pyridine
2-hexyloxyphenyl-5-(4-oxaoctyl)pyridine
2-hexyloxyphenyl-5-(4-oxanonyl)pyridine
2-hexyloxyphenyl-5-(4-oxadecyl)pyridine
2-hexyloxyphenyl-5-(4-oxaundecyl)pyridine
2-hexyloxyphenyl-5-(4-oxadodecyl)pyridine
2-hexyloxyphenyl-5-(4-oxa-6-methyloctyl)pyridine
2-p-butyloxyphenyl-5-(4-oxapentyl)pyridine
2-p-butyloxyphenyl-5-(4-oxahexyl)pyridine
2-p-butyloxyphenyl-5-(4-oxaheptyl)pyridine
2-p-butyloxyphenyl-5-(4-oxaoctyl)pyridine
2-p-butyloxyphenyl-5-(4-oxanonyl)pyridine
2-p-butyloxyphenyl-5-(4-oxadecyl)pyridine
2-p-butyloxyphenyl-5-(4-oxaundecyl)pyridine
2-p-butyloxyphenyl-5-(4-oxadodecyl)pyridine
2-p-butyloxyphenyl-5-(4-oxa-6-methyloctyl)-pyridine
2-p-ethoxyphenyl-5-(4-oxapentyl)pyridine
2-p-ethoxyphenyl-5-(4-oxahexyl)pyridine
2-p-ethoxyphenyl-5-(4-oxaheptyl)pyridine
2-p-ethoxyphenyl-5-(4-oxaoctyl)-pyridine
2-p-ethoxyphenyl-5-(4-oxanonyl)pyridine
2-p-ethoxyphenyl-5-(4-oxadecyl)pyridine
2-p-ethoxyphenyl-5-(4-oxaundecyl)pyridine
2-p-ethoxyphenyl-5-(4-oxadodecyl)pyridine
2-p-ethoxyphenyl-5-(4-oxa-6-methyloctyl)pyridine
2-p-methoxyphenyl-5-(4-oxapentyl)pyridine
2-p-methoxyphenyl-5-(4-oxahexyl)pyridine
2-p-methoxyphenyl-5-(4-oxaheptyl)pyridine
2-p-methoxyphenyl-5-(4-oxaoctyl)pyridine
2-p-methoxyphenyl-5-(4-oxanonyl)pyridine
2-p-methoxyphenyl-5-(4-oxadecyl)pyridine
2-p-methoxyphenyl-5-(4-oxaundecyl)pyridine
2-p-methoxyphenyl-5-(4-oxadodecyl)pyridine
2-p-methoxyphenyl-5-(4-oxa-6-methyloctyl)pyridine

Example 5

A mixture consisting of
3% of 2-p-hexyloxyphenyl-5-heptylpyridimine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine
7% of 2-p-hexyloxyphenyl-5-nonylpyrimidine,
23% of 2-p-nonyloxyphenyl-5-nonylpyrimidine,
28% of r-1-cyano-cis-4-(4'-octyloxybiphenyl-4-yl)-1-butylcyclohexane,
14% of r-1-cyano-cis-4-(4'-heptylbiphenyl-4-yl)-1-hexylcyclohexane,
6% of r-1-cyano-cis-4-(trans-4-pentylcyclohexyl)-1-(trans-4-pentylcyclohexyl)cyclohexane and
10% of chiral 2-p-n-octyloxyphenyl-5-(3-fluorononyl)-pyridine
has C< −20 $S_c^*$ 76 $S_A$ 84 Ch 97 I, a spontaneous polarization of 11.3 nC/cm$^2$ at 20° and a switching time of 150 μs at 15 V/μm.

Example 6

If the chiral pyridine in the mixture from Example 5 is replaced by 10% of chiral 2-p-octyloxyphenyl-5-(3-pentanoyloxybutyl)pyridine, the ferroelectric mixture obtained has $S_c^*$ 66 $S_A$ 72 Ch 88 I, a spontaneous polarization of 8.5 nC/cm$^2$ at 20° and a switching time of 170 μs at 15 V/μm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A chiral, tilted, smectic liquid crystalline phase comprising at least two liquid crystalline components, wherein at least one component is a compound of the formula Ic

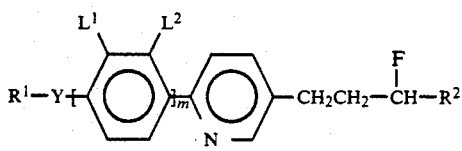

wherein
$R^1$ and $R^2$ each independently are alkyl, alkenyl or oxaalkyl having up to 12 C atoms;
$L^1$ and $L^2$ each independently are H or F,
Y is —O—, —CO—O—, —CO—O or a single bond, and m is 1 or 2.

2. A heterocycle according to claim 1, which is optically active.

3. A electrooptical display element comprising a liquid crystalline dielectric, wherein the dielectric is a phase according to claim 2.

4. A phase according to claim 2, wherein $R^1$ is straight-chain alkyl having 2 to 12 C atoms.

5. A phase according to claim 2, wherein Y is —O—.

6. A phase according to claim 2, wherein m is 1.

7. A phase according to claim 6, wherein

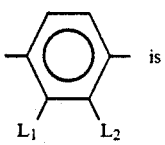 is

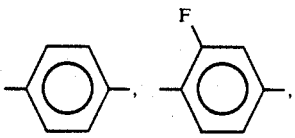,

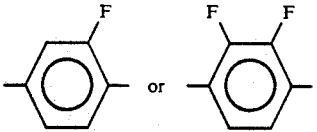 or

8. A phase according to claim 7, wherein the compound of the formula Ic is:
2-p-octyloxyphenyl-5-(3-fluorononyl)pyridine,
2-p-octyloxyphenyl-5-(3-fluorobutyl)pyridine,
2-p-octyloxyphenyl-5-(3-fluoropentyl)pyridine,
2-p-octyloxyphenyl-5-(3-fluorohexyl)pyridine,
2-p-octyloxyphenyl-5-(3-fluoroheptyl)pyridine,
2-p-octyloxyphenyl-5-(3-fluorooctyl)pyridine,
2-p-octyloxyphenyl-5-(3-fluorodecyl)pyridine,
2-p-octyloxyphenyl-5-(3-fluoroundecyl)pyridine,
2-p-octyloxyphenyl-5-(3-fluorododecyl)pyridine,
2-p-octyloxyphenyl-5-(3-fluorobutyl)pyridine,
2-p-hexyloxyphenyl-5-(3-fluoropentyl)pyridine,
2-p-hexyloxyphenyl-5-(3-fluorohexyl)pyridine,
2-p-dexyloxyphenyl-5-(3-fluorododecyl)pyridine,
2-p-dexyloxyphenyl-5-(3-fluoro-4-methylpentyl)pyridine,
2-(3-fluoro-4-octyloxyphenyl)-5-(3-fluorobutyl)pyridine,
2-(3-fluoro-4-octyloxyphenyl)-5-(3-fluoropentyl)pyridine,
2-(3-fluoro-4-octyloxyphenyl)-5-(3-fluorohexyl)pyridine,
2-(3-fluoro-4-octyloxyphenyl)-5-(3-fluoroheptyl)pyridine,
2-(3-fluoro-4-octyloxyphenyl)-5-(3-fluorooctyl)pyridine,
2-(3-fluoro-4-octyloxyphenyl)-5-(3-fluorononyl)pyridine,
2-(3-fluoro-4-octyloxyphenyl)-5-(3-fluorodecyl)pyridine,
2-(3-fluoro-4-octyloxyphenyl)-5-(3-fluoroundecyl)pyridine,
2-(3-fluoro-4-octyloxyphenyl)-5-(3-fluorododecyl)pyridine,
2-(3-fluoro-4-octyloxyphenyl)-5-(3-fluoro-4-methylpentyl)pyridine,
2-(2,3-difluoro-4-octyloxyphenyl)-5-(3-fluorobutyl)pyridine,
2-(2,3-difluoro-4-octyloxyphenyl)-5-(3-fluoropentyl)pyridine,
2-(2,3-difluoro-4-octyloxyphenyl)-5-(3-fluorohexyl)pyridine,
2-(2,3-difluoro-4-octyloxyphenyl)-5-(3-fluoroheptyl)pyridine,
2-(2,3-difluoro-4-octyloxyphenyl)-5-(3-fluorooctyl)pyridine,
2-(2,3-difluoro-4-octyloxyphenyl)-5-(3-fluorononyl)pyridine,
2-(2,3-difluoro-4-octyloxyphenyl)-5-(3-fluorodecyl)pyridine,
2-(2,3-difluoro-4-octyloxyphenyl)-5-(3-fluoroundecyl)pyridine,
2-(2,3-difluoro-4-octyloxyphenyl)-5-(3-fluorododecyl)pyridine, or
2-(2,3-difluoro-4-octyloxyphenyl)-5-(3-fluoro-4-methyl-pentyl)pyridine,

* * * * *